(12) United States Patent
Narmoneva et al.

(10) Patent No.: US 10,188,858 B2
(45) Date of Patent: Jan. 29, 2019

(54) METHOD AND DEVICE FOR TREATING A TISSUE WITH A HIGH FREQUENCY ELECTROMAGNETIC FIELD

(71) Applicant: University of Cincinnati, Cincinnati, OH (US)

(72) Inventors: Daria Narmoneva, Cincinnati, OH (US); Andrei Kogan, Cincinnati, OH (US); Abdul Sheikh, New Haven, CT (US); Toloo Taghian, Cincinnati, OH (US)

(73) Assignee: University Of Cincinnati, Cincinnati, OH (US)

( * ) Notice: Subject to any disclaimer, the term of this patent is extended or adjusted under 35 U.S.C. 154(b) by 0 days.

(21) Appl. No.: 14/490,584

(22) Filed: Sep. 18, 2014

(65) Prior Publication Data

US 2015/0080784 A1 Mar. 19, 2015

Related U.S. Application Data

(60) Provisional application No. 61/879,268, filed on Sep. 18, 2013.

(51) Int. Cl.
*A61N 1/06* (2006.01)
*A61N 1/32* (2006.01)
*A61N 1/40* (2006.01)

(52) U.S. Cl.
CPC ............. *A61N 1/326* (2013.01); *A61N 1/06* (2013.01); *A61N 1/40* (2013.01)

(58) Field of Classification Search
CPC ........ A61B 18/18; A61N 1/06; A61N 1/0468; A61N 1/326; A61N 1/40
See application file for complete search history.

(56) References Cited

U.S. PATENT DOCUMENTS

| | | | |
|---|---|---|---|
| 5,489,437 A | * | 2/1996 | Marra ................ A61L 15/28 424/443 |
| 6,058,331 A | | 5/2000 | King |
| 6,334,069 B1 | | 12/2001 | George et al. |
| 6,988,004 B2 | | 1/2006 | Kanno et al. |
| 7,341,062 B2 | | 3/2008 | Chachques et al. |
| 7,483,749 B2 | | 1/2009 | Leonhardt et al. |

(Continued)

OTHER PUBLICATIONS

Tanner, Alan J., transcript of interview, "Healing wounds with microwaves and histamine", taken from Keely Net BBS, Sponsored by Vangard Sciences, Mar. 19, 1980 <http://www.totse2.com/totse/en/fringe/fringe_science/heal1.html> (pp. 1-4).

(Continued)

*Primary Examiner* — Amanda Hulbert
*Assistant Examiner* — Natasha Patel
(74) *Attorney, Agent, or Firm* — Wood Herron & Evans, LLP

(57) ABSTRACT

Methods and systems for treating a tissue with a high frequency electric field to activate MAPK/ERK pathways, induce angiogenesis, induce angionenic factos such as NO and VEGF, or promote wound healing. Aspects of the invention are directed to methods of treating chronic wounds such as diabetic ulcers and hypoxia induced wounds. Aspects utilize high frequency electric field having a frequency in the GHz range, and preferably between about 1 GHz and about 10 GHz.

20 Claims, 14 Drawing Sheets

(56) References Cited

U.S. PATENT DOCUMENTS

| | | |
|---|---|---|
| 7,520,549 B2 | 4/2009 | Leighton |
| 7,584,003 B2 | 9/2009 | Zanella |
| 7,747,328 B2 | 6/2010 | Chandler et al. |
| 7,981,611 B2 | 7/2011 | Brighton |
| 7,991,466 B2 | 8/2011 | Blum et al. |
| 8,034,014 B2 | 10/2011 | Higgins et al. |
| 8,401,668 B2 | 3/2013 | Deem et al. |
| 2001/0044643 A1* | 11/2001 | Litovitz ............... A61N 1/40 607/100 |
| 2003/0216729 A1* | 11/2003 | Marchitto ............ A61B 18/14 606/41 |
| 2008/0237028 A1* | 10/2008 | Kislev ................. A61B 8/481 204/157.15 |
| 2010/0114086 A1 | 5/2010 | Deem et al. |
| 2010/0274177 A1* | 10/2010 | Rybski ............... A61M 1/0088 604/20 |
| 2011/0142907 A1* | 6/2011 | Marchitto ............ A61L 24/001 424/426 |
| 2011/0213319 A1* | 9/2011 | Blott .................. A61F 13/0216 604/291 |
| 2013/0123764 A1* | 5/2013 | Zarsky ................. A61B 18/18 606/13 |
| 2015/0080784 A1 | 3/2015 | Narmoneva et al. |

OTHER PUBLICATIONS

Sheikh, Abdul Q., et al., "Regulation of endothelial MAPK/ERK signaling and capillary morphogenesis by low-amplitude electric field", J.R. Soc. Interface, published online, doi:10.1098/rsif.2012/0548 (pp. 1-15).

Schramm, J. Mark, et al., "A Unique Combination of Infrared and Microwave Radiation Accelerates Wound Healing", Plastic and Reconstructive Surgery, Jan. 2003, <http://journals.lww.com/plasreconsurg/Abstract/2003/01000/A_Unique_Combination_ofInfrared_and_Microwave.44.aspx> (pp. 258-266).

Korpan Nikolai M., et al., "Clinical Effects of Continuous Microwave for Postoperative Septic Wound Treatment: A Double-Blind Controlled Trial", The American Journal of Surgery, vol. 170, Sep. 1995 <http://www.sciencedirect.com/science/article/pii/S0002961005800133> (pp. 271-276).

Korpan, Nikolai M., et al., "Continuous Microwave Enhances the Healing Process of Septic and Aseptic Wounds in Rabbits", Journal of Surgical Research, vol. 57 No. 6, Dec. 1994 (pp. 667-671).

\* cited by examiner

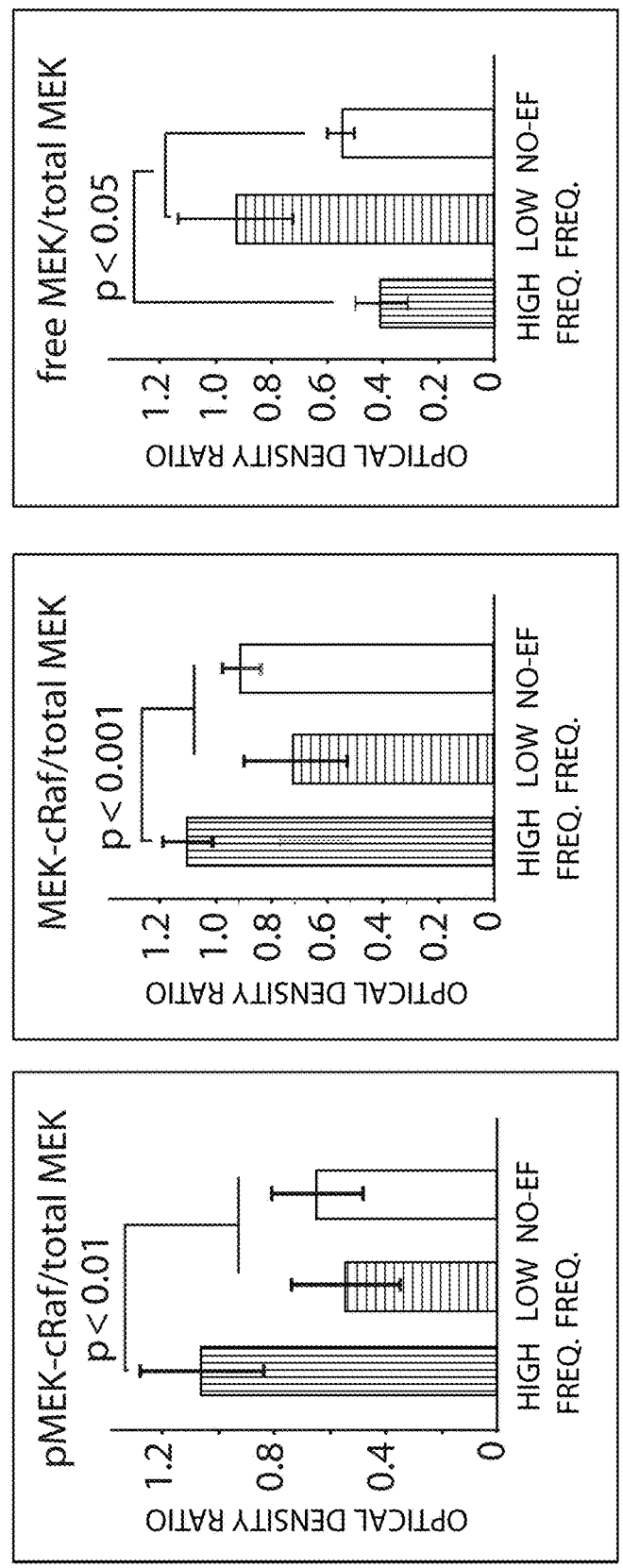

US 10,188,858 B2

METHOD AND DEVICE FOR TREATING A TISSUE WITH A HIGH FREQUENCY ELECTROMAGNETIC FIELD

RELATED APPLICATION

The Present application claims priority to U.S. Ser. No. 61/879,268 filed Sep. 18, 2013, the disclosure of which is hereby incorporated herein by reference in its entirety.

FIELD OF THE INVENTION

The present invention relates to methods of treating a tissue with a high frequency electromagnetic field, and more particularly to treating wounds, inducing angiogenesis, increasing the expression of angiogenic factors, NO, and/or VEGF and/or inducing MAPK activity in tissues with a high frequency electromagnetic field.

BACKGROUND OF THE INVENTION

In the United States, the occurrence of diabetes is on the rise. Major complications of diabetes include diabetic ulcers and amputation of the lower extremities. Diabetic ulcers precede the vast majority of diabetic amputations. Diabetic ulcers are thought to proceed due to micro and macro vascular complications that result in hypoxia and compromise the natural wound healing processes of the tissues in the affected limbs. As a result, the natural wound healing processes are unable to repair damaged tissue in ulcerative diabetic patients. Diabetic ulcers are an example of chronic wounds and hypoxia induced wounds. Treatments for diabetic ulcers, chronic wounds, and hypoxia induced wounds are needed.

Currently available treatments for chronic wounds that are the result of hypoxia and/or compromised wound healing processes typically include the use of therapies that attempt to replace the extracellular matrix in the wound to provide scaffolding on which healing can occur. Currently therapies typically employ advanced moist wound therapy techniques, control of infection, bioengineered tissue or skin substitutes, growth factors, and negative pressure therapy. However, each of these therapies has drawbacks that limit their use.

Therapeutic processes for improving healing of chronic wounds, hypoxia induced wounds, and diabetic ulcers are needed.

Endogenous physiological (40-250 mV/mm) electric field is an important component of the body's wound healing response. Different types of low, physiological amplitude electromagnetic field have been shown to influence a wide variety of biological systems and have been used as a therapeutic tool for tissue repair, including bone healing, soft tissue repair and the healing of chronic wounds. However, the widespread acceptance of electric field (EF) therapies for wound healing has not been adopted, and it is understood that no FDA-approved device for wound healing exists yet.

SUMMARY OF THE INVENTION

Aspects of the invention are directed to methods and systems for improving wound healing in the tissues of a subject, especially in the healing of chronic wounds such as diabetic ulcers and bed sores that result from the vascular changes caused by diabetes or other hypoxia inducing conditions or other conditions that compromise the tissues natural wound healing processes.

An embodiment of the invention is directed to methods of treating wounds in a tissue of a subject that includes exposing the tissue to a high frequency electric field for a period of time to induce wound healing. Exemplary wounds include chronic wounds such as diabetic wounds, bed sores, and hypoxia induced wounds. Other wounds wherein angiogenesis, expression of angiogenic factors such as NO and VEGF or induction of the MAPK/ERK pathways would be beneficial may be treated by these methods as well.

BRIEF DESCRIPTION OF THE DRAWINGS

The accompanying figures, which are incorporated in and constitute a part of this specification, illustrate exemplary embodiments of the invention and, together with a general description of the invention given above, and the detailed description given below, serve to explain the principles of the invention.

FIG. 8A is a graph demonstrating that high frequency EF significantly increased phosphorylated MEK-cRAF complex.

FIG. 8B is a graph demonstrating that high frequency EF did not change the total concentration of MEK-cRAF.

FIG. 8C is a graph demonstrating that high frequency EF significantly decreased free MEK compared to the low frequency EF and control.

DETAILED DESCRIPTION OF THE INVENTION

Figure 1A:
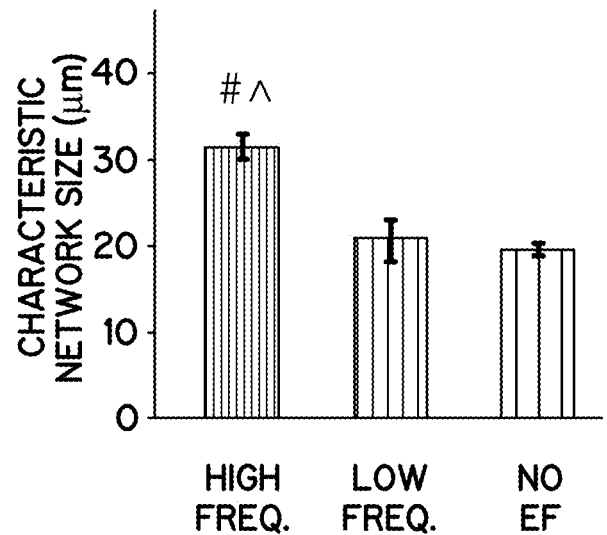
FIG. 1A is a graph demonstrating that high frequency EF (7.5 GHz) enhances angiogenic response by microvascular cells when compared with low frequency EF (60 Hz) or no EF control.

An aspect of the invention is based on the surprising discovery that high frequency electric fields, i.e., fields having a frequency of at least 1 GHz and a physiological amplitude applied to a tissue in a non-thermal manner can promote wound healing. It was also discovered that such high frequency electric fields can activate the mitogen-activated protein kinase (MAPK) and extracellular signal-regulated kinase (ERK) pathways, as well as stimulate expression of angiogenic factors such as NO and VEGF in wound cells and tissues. Without being bound to a particular theory, the high frequency electric field can penetrate the cell membrane to mediate intracellular signaling, whereas low frequency electric fields, i.e., in the megahertz range or less, are limited to the cell membrane. Accordingly, aspects of the invention are directed to method of treating the tissue of a subject with a high frequency electromagnetic field to achieve at least one of these results. An embodiment is directed to methods of treating wounds in a tissue of a subject that includes exposing the tissue to a high frequency electromagnetic field for a period of time to induce wound healing. Exemplary wounds include chronic wounds such as diabetic ulcers, bed sores, and hypoxia induced wounds. Other wounds wherein angiogenesis, expression of angiogenic mediators NO, VEGF, or induction of the MAPK/ERK pathways would be beneficial may be treated by these methods as well.

Another embodiment of the invention is directed to methods of inducing angiogenesis in a tissue of a subject that includes exposing the tissue to a high frequency electromagnetic field at a frequency and for a period of time sufficient to induce angiogenesis. The induced angiogenesis improves healing of wounds, including the healing of chronic wounds.

Another embodiment of the invention is directed to methods of inducing MAPK/ERK pathway activation in a tissue of a subject that includes exposing the tissue to a high frequency electromagnetic field at a frequency and for a period of time sufficient to induce MAPK/ERK pathway activation.

Another embodiment of the invention is directed to methods of inducing VEGF expression in a tissue of a subject that includes exposing the tissue to a high frequency electromagnetic field at a frequency and for a period of time sufficient to induce VEGF expression.

Another embodiment of the invention is directed to methods of inducing NO expression in a cell or tissue of a subject that includes exposing the tissue to a high frequency electromagnetic field at a frequency and for a period of time sufficient to induce VEGF expression.

Embodiments of the invention utilize a high frequency electric field that is at least a 1 GHz electric field. Alternative embodiments utilize a high frequency electric field that is in a range from about 1 GHz to about 10 GHz and preferably in a range from about 5 GHz and 8 GHz. In another embodiment, the high frequency electric field is about 7.5 GHz.

The high frequency electric fields are typically applied to the tissue over a range from about 100 mV mm$^{-1}$ to about 300 mV mm$^{-1}$, however, in certain embodiments, amplitudes outside of this range may be employed. In alternative embodiments, the high frequency electric field are applied to the tissues over a range from about 150 mV mm$^{-1}$ to about 250 mV mm$^{-1}$ and preferably, the high frequency electric field is applied to the tissue at about 200 mV mm$^{-1}$.

The high frequency electric field is applied to the tissue for a period of time sufficient to result in at least one of activation of the MAPK/ERK pathway in cells of the tissue, induce angiogenesis in the tissue, increase the expression of angiogenic mediators such as NO and/or VEGF, and promote wound healing in the tissue. In an embodiment, the tissue is exposed to a high frequency electric field for a duration of at least 20 minutes per day. The term day is understood to mean a 24 hour cycle. In another embodiment, the tissue is exposed to the high frequency electric field for at least 60 minutes per day, or at least 2 hours per day, or between 1 hour per day and 24 hours per day.

The tissue being treated may be exposed continuously over the desired duration of time per day, or the desired duration may be administered over smaller intervals during the day. The tissue may be exposed for as little as 1 day, or over the course of several days, a week, two weeks, a month or more, or even years as may be necessary to treat the tissue or induce the MAPK/ERK pathway or induce expression of angiogenic mediators such as NO and/or VEGF in a subject. In an embodiment, the tissue is treated for up to 12 weeks.

The high frequency electric field is delivered to the tissue by at least one antenna, and in an alternative embodiment, two antennas, capable of applying the high frequency electric field to the tissue. The antenna creates a field of desired strength in the close proximity to the conducting elements (the near-field evanescent modes) and limits its radiative output to ensure control of the exposed tissue areas. This is accomplished by appropriately arranging the spacing and geometric shape of the signal and ground paths of the antenna and can be scaled to arrays of antennas that form a planar source of the field. The antenna is coupled to a high frequency electric field source sufficient to produce the desired frequency of electric field, such as an oscillator like the 8350B Sweep Oscillator from Agilent Technologies. A dedicated low-cost oscillator can be integrated with the antenna for commercial use.

During use, the at least one antenna is placed in close proximity to the tissue being treated such that the tissue is exposed to the high frequency electric field. The at least one antenna does not contact the tissue. In an embodiment, the at least one antenna is positioned near the tissue with a distance in a range from about 1 mm to about 20 mm between the tissue and the least one antenna. In another embodiment, the distance between the antenna and the surface of the tissue is in a range from about 3 mm and to about 10 mm. In another embodiment, the distance between the antenna and the surface of the tissue is about 5 mm. The antenna may be separated from the wound by a dressing, and in an embodiment, the antenna may form a part of the dressing.

The at least one antenna can induce at least one of wound healing, angiogenesis, expression of angiogenic mediators such as NO, VEGF, and MAPK/ERK pathway activation in a tissue of a subject even if the tissue is covered by a dressing or other wound healing treatment such as a hydrogel. Indeed, the combination of covering a wound with a dressing, and preferably a hydrogel dressing, can further improve the wound healing An embodiment of the invention is directed to inducing at least one of wound healing, angiogenesis, expression of angiogenic mediators such as NO, VEGF, and MAPK/ERK pathway activation in a tissue of a subject wherein the tissue is covered by a dressing or other wound healing treatment such as a hydrogel.

EXAMPLE

Methods Used in Example
Microvascular Endothelial Cell Isolation and Culture
Murine microvascular endothelial cells were isolated from the lungs of C57 mice (Jackson Laboratory, Maine, USA) as described previously. Cells were doubly sorted using PECAM-1- and ICAM-2-conjugated magnetic beads (Invitrogen Corporation, CA, USA) and cultured in medium M199 (HyClone, UT, USA) supplemented with 10% fetal bovine serum (FBS; Atlanta Biologicals, GA, USA), 1% antibiotic/antimycotic (AB/AM; Atlanta Biologicals, USA), 1% heparin (Sigma-Aldrich, MO, USA) and 10ng/mL endothelial growth factor supplement (Sigma-Aldrich, MO, USA). Cells from passages 4-9 were used. All experiments were conducted in the culture medium (medium M199, 10% FBS, 1% antibiotic/antimycotic and 1% heparin) without additional growth factor supplementation.

In Vitro EF Exposure Setup
A high-frequency and a low-frequency setup were built to allow cell exposure to EF with a well-characterized field distribution, which was confirmed for each frequency by numerical simulations, as described below.

High frequency EF setup: A custom setup was built which allowed EF exposure operating at 7.5 GHz frequency. This frequency represents the regime where the membrane impedance becomes low (dielectric behavior), resulting in the field penetration across the membrane. The high frequency EF setup operated in Transverse Magnetic mode (TM010), where the dominant electric field was normal to the plane of the cultured cells, and the magnetic field at the location of the cells is approximately zero. The apparatus consists of a cylindrical cavity resonator made from a copper waveguide with length=31.9 mm and diameter=31.7 mm. The cavity resonator was placed in a temperature controlled 5% $CO_2$ cell culture incubator and connected to a semi-rigid coax (Microcoax, PA, USA) transmission line supplying 7.5 GHz EF from a Vector Network Analyzer (Anritsu, CA, USA). Cells were seeded in 12 mm diameter culture insert (Millipore, MA, USA), which was placed in a small plastic dish filled with the culture medium (20 mm in diameter) located inside the cavity resonator. This dish was connected to a large reservoir outside the resonator to ensure a constant medium level. Once coupled, a frequency sweep of the reflected power showed a dip that occurred when the frequency matched the resonant frequency of the cavity (7.5 GHz). Under these critical coupling conditions, the reflected signal on resonance dropped, and >90% power supplied by the coaxial was used to support the oscillating cavity mode (TM010). The quality factor (Q) of the cavity was 170, and the calculated field intensity for the setup with the insert without cells was 156 mV/mm, which is in physiological range.

Low frequency EF setup: The custom built setup used for low frequency (60 Hz) EF exposure consisted of a parallel plate capacitor (135 mm×128 mm, 26 mm apart)assembled in the same cell culture incubator. This frequency is within the range where intracellular space is shielded by the applied field; and where the angiogenic effects of EF have been previously observed. The plates of the capacitor were connected to an Agilent 33250A Function/Arbitrary Waveform generator (Agilent Technologies, Inc., CA, USA) and an oscilloscope (Tektronix Inc., OR, USA). Endothelial cells were seeded in the culture insert, which was placed in a small dish located between the plates. The electric field was normal to the cell plane, and the calculated field intensity for the setup with the insert without cells was within physiological range (209 mV/mm).

Numerical calculation of the electric field distribution: A detailed numeric calculation of the electric field distribution in the high frequency resonator and the low frequency capacitor was performed using an accurate three-dimensional model of the apparatus and the sample insert using ANSYS HFSS package (ANSYS, PA, USA). The simulation program calculated a solution of the Maxwell's equations using measured dimensions of the dielectric insert and the media container and inputs (microwave power and the capacitor excitation voltage). Independence of the software output of the grid density was ensured by performing multiple calculations on grids of different sizes and densities. Results demonstrated that the electric field distributions at the location of the cells were within the physiological range and similar for both setups, as well as uniform in the central part of the insert. The upper bound for the field power specific absorption rate (SAR) for the sample in the resonator was estimated for the assumption that all of the field power fed to the resonator (50 µW in all experiments reported here) is absorbed in the sample. Under these "worst case" assumptions which significantly overestimate the absorption rate, the SAR value is at most 0.1 W/kg, which is considerably lower than the SAR human health safety limit.

Temperature measurements: For temperature measurements, EF exposure was briefly stopped, and the recordings of the temperature in the culture medium were made using an infrared thermometer (Braun, OH, USA, 0.2° C. accuracy) without taking the samples out of the exposure setup. To confirm the accuracy of the temperature measurements, the following controls were included. First, a control sample was placed inside the same incubator as the EF exposure apparatus, but was not subjected to EF stimulation. Second, the temperature of a large medium reservoir located in the same incubator was measured. All measurements were performed in duplicates and experiments were repeated three times. The results demonstrate that the average temperature of all samples did not change during EF exposure and remained within 37±0.12 degree interval with 95% confidence.

In Vitro EF Experiments

Capillary morphogenesis, and MAPK pathways activation were quantified following 12 hours of EF exposure, and the analyses of VEGF expression, cell proliferation and apoptosis were conducted up to 24 hours of EF exposure. The experimental groups included endothelial cells exposed to high frequency EF, low frequency EF and a group not exposed to EF.

In Vitro Capillary Morphogenesis

Capillary morphogenesis was assessed using nanofiber-based angiogenesis assay previously developed in the lab, in which endothelial cells seeded on RAD16-II peptide nanofiber hydrogel (SynBioSci Corporation, CA, USA) undergo spontaneous capillary morphogenesis with clearly identifiable lumens in the absence of external angiogenic growth factors. Endothelial cells were seeded on the surface of 1% (w/v) hydrogel in cell culture inserts (Millipore, MA, USA) at a seeding density of $10^5$ cells/cm$^2$. Cells seeded on 5% gelatin-coated inserts were used as a negative control. Cells were labeled with CellTracker dye (Invitrogen, USA) before seeding or with Phalloidin-TRITC (Sigma Aldrich, St Louis, Mo., USA). After EF exposure, samples (at least N=10 separate EF exposure experiments per group) were fixed with 2% formaldehyde, and images of the sample surface (n=5 per sample) were captured at 20× magnification using an inverted fluorescent microscope (Olympus IX81; Olympus, Pa., USA). The characteristic size of capillary-like networks was determined using correlation analysis and custom-written MATLAB code (The Math Works, MA, USA).

Cell Proliferation and Apoptosis

Cells were seeded (2×10$^4$ cells/cm$^2$) on 5% gelatin-coated culture inserts (Millipore, MA, USA). Some samples were incubated with bromodeoxyuridine (BrdU; Invitrogen, USA) for 8 hrs prior to experiments. After 12 and 24 hours of EF exposure, cells were immediately fixed (2% formaldehyde) and stained with either anti-BrdU antibody (Invitrogen, USA) or with anti-active Caspase-3 antibody (Promega, WI, USA) followed by goat anti-rabbit Alexa Fluor 594 and DAPI nuclear staining (both from Invitrogen, USA) to identify proliferating and apoptotic cells, respectively. Percentages of proliferating or apoptotic cells were determined from five images at 20× magnification per sample. For each assay, experiments were repeated four times.

VEGF and PlGF Protein Expression

VEGF and PlGF are two major angiogenic cytokines acting through VEGF receptors pathway. VEGF binds to both VEGFR1 and VEGFR2 receptors, although signals through VEGFR2. In contrast, PlGF which only binds to and signals through VEGFR1. To determine the effect of EF on the VEGF and PlGF protein release by endothelial cells, culture medium samples (at least N=6 separate experiments) were used to measure VEGF and PlGF protein levels using appropriate ELISA kits (R&D Systems, MN, USA).

ERK, JNK, p38 MAPK Pathways Activation

After EF exposure, cells were lysed using buffer containing 20 mM Tris-HCl, 150 mM NaCl, 1 mM Na2EDTA, 1 mM EGTA, 1% Triton, 2.5 mM sodium pyrophosphate, 1 mM beta-glycerophosphate, 1 mM Na$_3$VO$_4$, 1 µg/ml leupeptin and 1 mM phenylmethylsulfonyl fluoride (PMSF). The total protein concentration in each sample lysate was determined using CoomassiePlus Assay Kit (Thermo Fisher Scientific, IL, USA). 10 µg of total protein was used for all MAPK pathway ELISAs. The total and phosphorylated levels of ERK, MEK, p38 and JNK proteins were quantified using appropriate sandwich ELISA kits (Cell Signaling Technology, MA, USA). MEK-cRaf complex levels and free (unbound) MEK levels were quantified according to previously described protocols with modifications. The total MEK levels are presented in optical densities and phosphorylated MEK, MEK-cRaf and pMEK-cRaf levels are normalized to total MEK levels. For negative control, β-actin (Invitrogen, USA) was immunoprecipitated from the lysate and subjected to ELISAs. All ELISA assays were performed in duplicates or triplicates, with all experiments repeated at least N=6 times.

Inhibitor Studies

To determine the role of VEGF signaling in EF-mediated angiogenic responses, experiments were repeated in the presence of 0.1 µg/mL soluble anti-mouse VEGF blocking antibody (R&D Systems, MN, USA), or 5 µM SU5416 (Sigma-Aldrich, MO, USA), a specific pharmacological VEGFR2inhibitor, or in the presence of 10 µM U0126 MEK inhibitor (Sigma-Aldrich, MO, USA). The efficiency of SU5416 has been verified using a standard approach of inducing MEK activation by 20 ng/mL VEGF and then inhibiting the response with SU5416. To examine the role of PI3K, Ca$^{2+}$ and eNOS signaling in EF-mediated MEK activation, cells were treated with 10 µM LY294002 (PI3K inhibitor), 10 µM BAPTA (Ca$^{2+}$ chelator), or 200 µM Nω-Nitro-L-arginine methyl ester hydrochloride (L-NAME, eNOS inhibitor), respectively, and the total and phosphorylated MEK levels were measured using ELISA. All inhibitors were added to the culture supernatant and pre-incubated for one hour to equilibrate respective target blocking prior to EF exposure. All analyses were done in duplicates/triplicates, and all inhibitor experiments were repeated at least N=3 times.

In Vivo Diabetic Wound Healing Model and EF Treatment 8-10 weeks old female BKS.Cg-m+/+Leprdb/J (db/db) mice with serum glucose levels >450 mg/dL were used. Previous studies have shown that this animal model is characterized by a delayed wound healing, with reduced neovascularization of the repair tissue. Two full-thickness excisional skin wounds (8 mm) were created on the back of the mice, washed with 50 µl of sterile phosphate-buffered saline (PBS) and covered with sterile adhesive dressing (Tegaderm™, 3M, MN, USA). EF treatment of the wounds was achieved through a custom built EF exposure setup, which included two antennae connected to the EF source (8350B Sweep Oscillator, Agilent Technologies, CA, USA) through a flexible co-axial cable. Prior to exposure, the animals were anesthetized and EF antennas were placed approximately 5 mm away from the wounds. EF stimulation of 7.5 GHz and ~200 mV/mm was applied for one hour every day for 7 days. Control group included animals, which underwent the same wounding procedure, but were not exposed to EF (N=5 animals per group). All animals were sacrificed and wounds were harvested at day 8.

VEGF Expression in the Wounds

The harvested wounds where homogenized in 50 mM Tris-HCl buffer containing 1% NP40, aprotinin (3.3 µg/ml), leupeptin (10 µg/ml) and pepstatin (4 µg/ml). VEGF protein expression in wound tissue homogenate was measured using ELISA kit (R&D Systems, MN, USA).

Statistical Analyses

The results are reported as average±standard deviation. Multi-factor ANOVA and post-hoc tests with Bonferroni corrections (SPSS, IL, USA) were used to test for the effects of EF, field frequency and the inhibitors on the capillary morphogenesis, VEGF expression and total as well as phosphorylated levels of MAPK pathway proteins. Results were considered statistically significant at $p<0.05$.

Results

EF Enhances Angiogenic Response by Microvascular Endothelial Cells

Figure 1B:
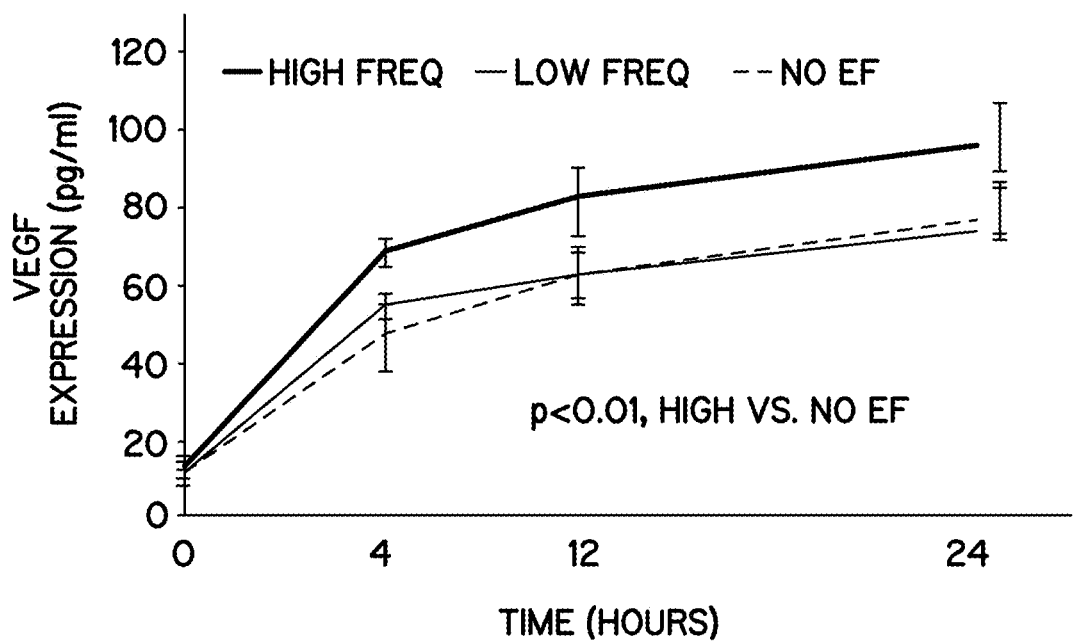
FIG. 1B is a graph demonstrating that high frequency EF (7.5 GHz) enhances VEGF expression by microvascular cells when compared with low frequency EF (60 Hz) or no EF control.
Figure 2A:
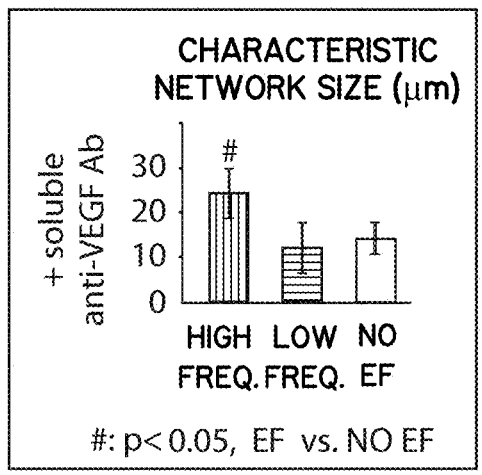
FIG. 2A is a bar graph demonstrating that the effects of EF on capillary morphogenesis and VEGF release into the medium were retained in the presence of a VEGFR2 blocking antibody (n=4, p<0.05) suggesting that EF-mediated stimulation of angiogenesis does not require VEGF ligand-receptor binding.
Figure 2B:
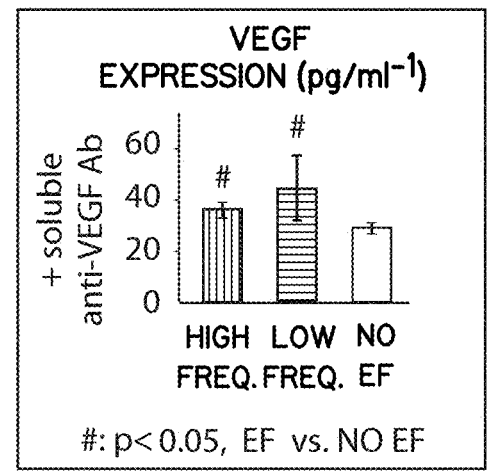
FIG. 2B is a graph demonstrating that the effects of EF on capillary morphogenesis and VEGF release into the medium were retained in the presence of a VEGFR2 blocking antibody (n=4, p<0.05) suggesting that EF-mediated stimulation of angiogenesis does not require VEGF ligand-receptor binding.
Figure 3A:
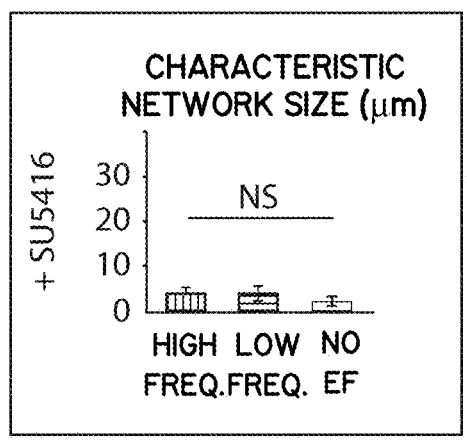
FIG. 3A is a graph showing that treatment of endothelial cells with a potent VEGFR2 inhibitor SU5416 effectively abolished capillary morphogenesis.
Figure 3B:
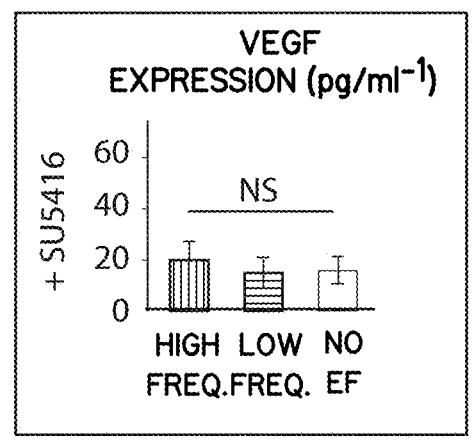
FIG. 3B is a graph showing that treatment of endothelial cells with a potent VEGFR2 inhibitor SU5416 effectively abolished VEGF release.
Figure 4A:
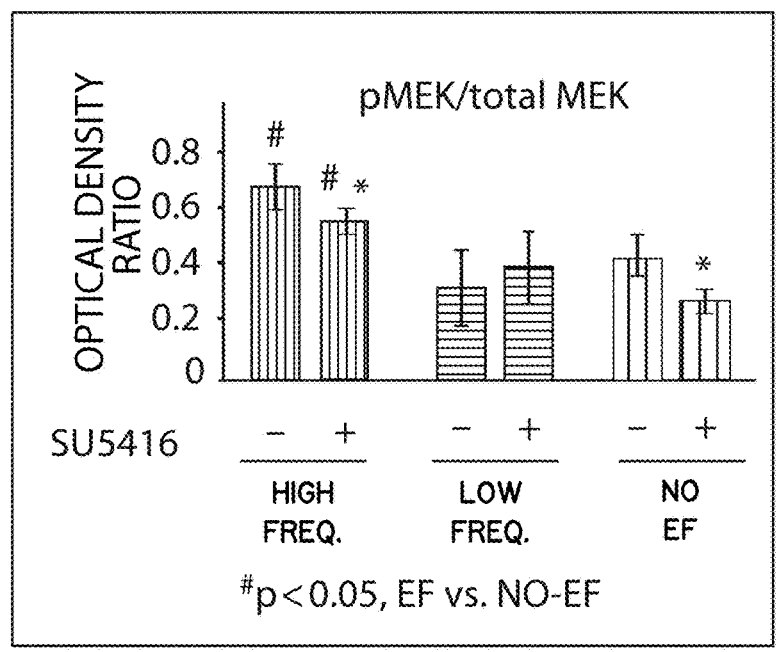
FIG. 4A is a graph showing that treatment of endothelial cells with a potent VEGFR2 inhibitor SU5416 did not block high frequency EF-induced MEK phosphorylation which was significantly higher than low frequency and no-EF controls even in the presence of SU5416.
Figure 4B:
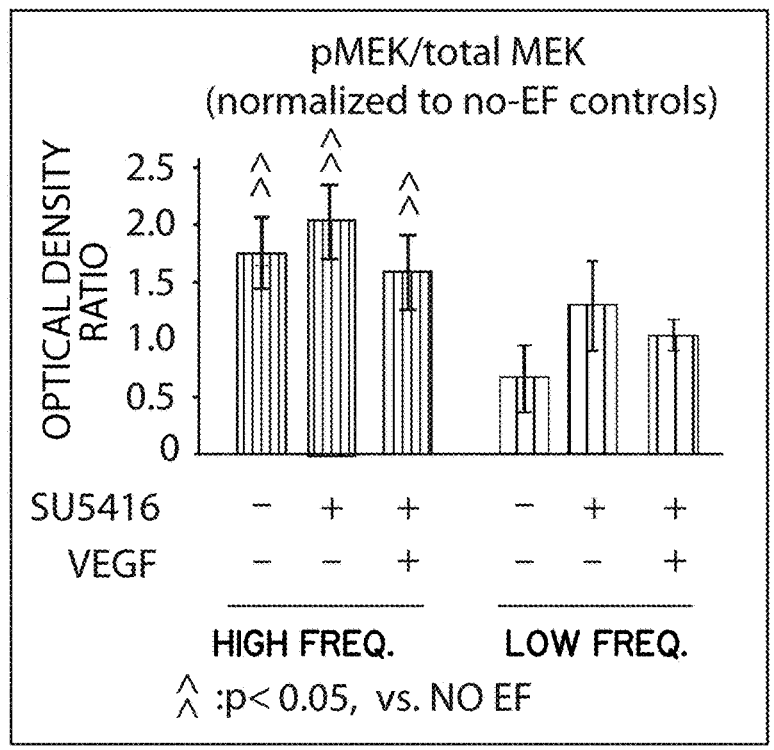
FIG. 4B is a graph demonstrating that high frequency EF-induced MEK phosphorylation which was significantly higher than low frequency and no-EF controls even in the presence of SU5416.

In the capillary morphogenesis assay used in this study, endothelial cells undergo spontaneous formation of multicellular capillary structures with clearly identifiable lumens by 12 hours of cell seeding on the nanofiber hydrogel. High frequency EF exposure resulted in significantly larger structures, as compared to low frequency and no-EF groups ($p<0.001$, FIG. 1A), while no significant differences between low frequency and no-EF groups were observed. Similarly, VEGF expression was significantly increased in cells exposed to high frequency EF, as compared to low frequency or no-EF groups ($p<0.001$, FIG. 1B), while there was no significant difference in VEGF levels between low frequency and no-EF groups. The pro-angiogenic effects of EF were not associated with EF-induced directional cell responses (electrotaxis), as demonstrated by the absence of cell re-orientation when seeded on the gelatin-coated inserts in this field configuration. Interestingly, the effects of EF on both capillary morphogenesis and VEGF released by endothelial cells were retained in the presence of soluble anti-VEGF blocking antibody ($p<0.05$, FIGS. 2A and 2B), as compared to no-EF group. An addition of potent VEGFR2 receptor inhibitor SU5416 completely abolished capillary morphogenesis and significantly reduced VEGF release in all experimental groups, including no-EF controls (FIGS. 3A and 3B). Next, we investigated the effects of EF on the signaling downstream of VEGFR2 by quantifying the phosphorylation of MEK, which is upstream of ERK. High frequency EF resulted in increased MEK phosphorylation, where the magnitude of the effect did not depend on the presence of SU5416 or exogenous VEGF and remained at the 1.5- to 2-fold levels (FIGS. 4A and 4B). This effect was not present in the low frequency group. These results suggest that external VEGF binding to its receptor may not be required for pro-angiogenic effects of EF in this system, and that the EF stimulation is not strong enough to reverse a complete inhibition of VEGFR2-mediated angiogenesis induced by SU5416. However, the EF-induced VEGFR2-independent activation of MEK/ERK pathway may be responsible for the increased release of VEGF observed in high-frequency group (FIG. 1B) and potentially activation of the VEGF autocrine loop.

Figure 5A:
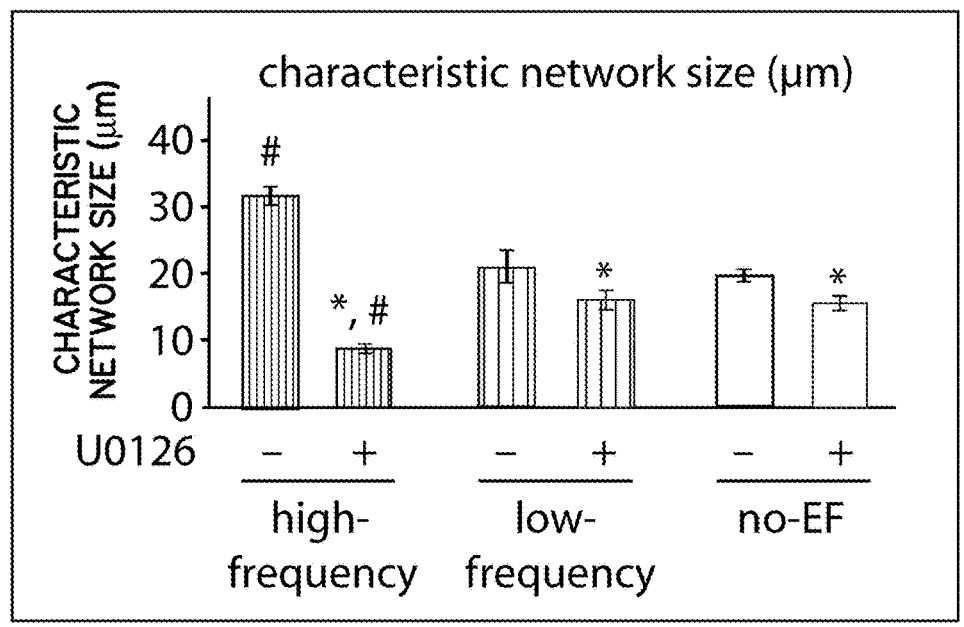
FIG. 5A is a graph demonstrating that treatment with MEK inhibitor U0126 decreased network size in all groups but to a greater extent in EF treated cells (n=5).
Figure 5B:
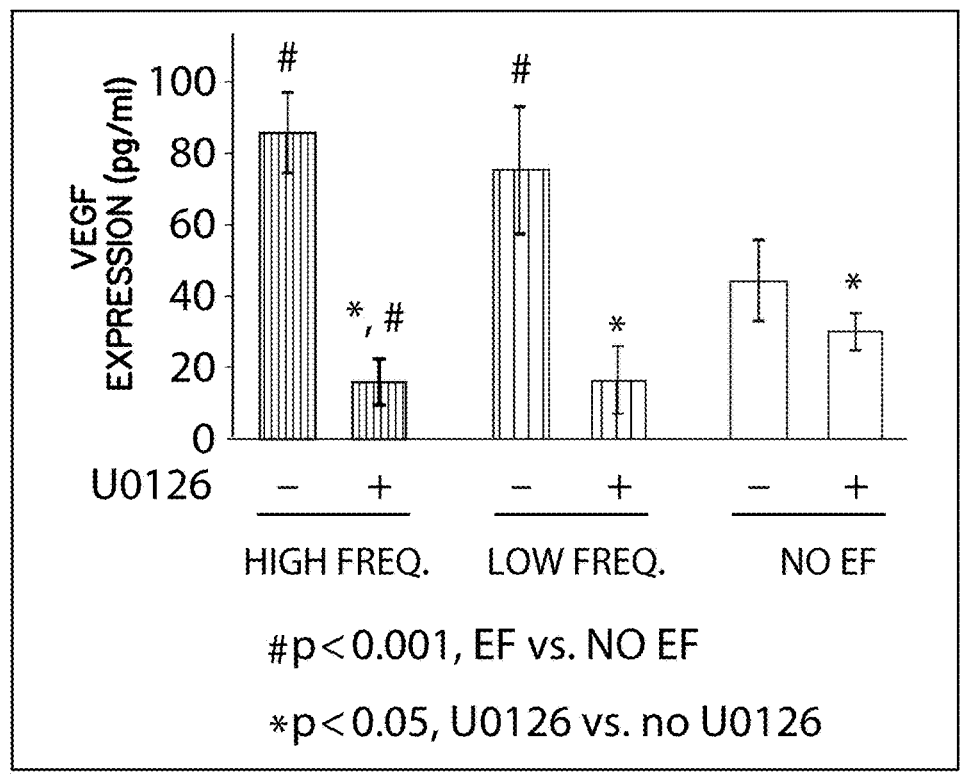
FIG. 5B is a graph demonstrating that treatment with MEK inhibitor U0126 decreased VEGF expression in all groups but to a greater extent in EF treated cells (n=4).

To further conform the involvement of MEK/ERK pathway in EF-mediated angiogenic responses, capillary morphogenesis and the VEGF release by endothelial cells were quantified in the presence of high affinity MEK inhibitor U0126. These responses were significantly reduced in all experimental groups, as compared to no inhibitor controls ($p<0.05$, FIGS. 5A and 5B). Interestingly, treatment with U0126 effectively reversed the effect of high frequency EF on capillary morphogenesis and VEGF release, where significantly lower values for characteristic network size and VEGF release were observed, as compared to those in low frequency EF and no-EF groups ($p<0.001$). There was no significant difference in network size between low frequency EF and no-EF groups in the presence of U0126. There was no effect of EF exposure on PlGF release by endothelial cells as compared to no-EF group.

High frequency EF increases ERK, but not JNK or p38 phosphorylation in endothelial cells.

Figure 6A:
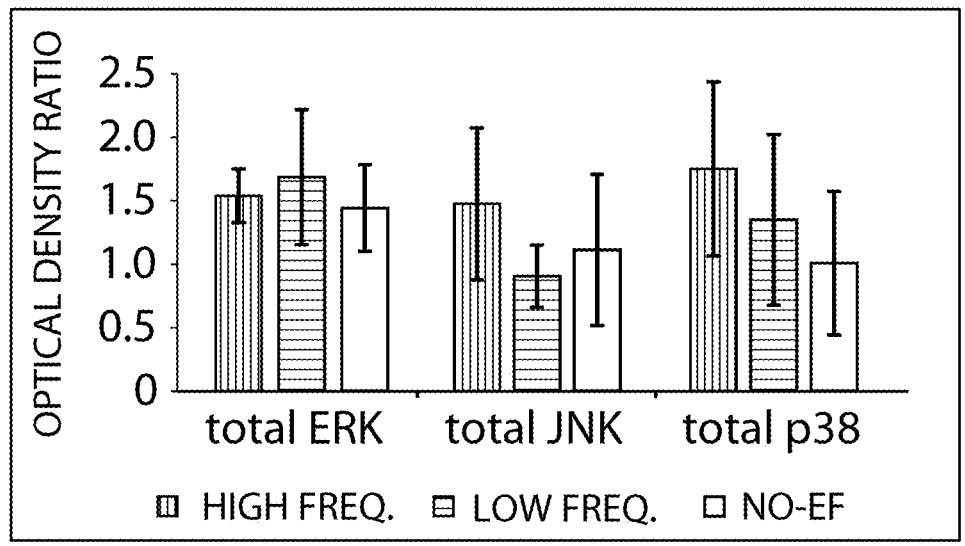
FIG. 6A is a graph demonstrating that high frequency EF did not alter total protein concentrations for ERK, JNK, or p38.

Both high frequency and low frequency EF did not affect the total levels of ERK, JNK or p38 protein expression (FIG. 6A). However, cell exposure to high frequency EF resulted in significantly increased levels of ERK phosphorylation, as compared to no-EF group ($p<0.001$, FIG. 6B), while no significant effects of high frequency EF on JNK and p38 phosphorylation were observed. Also, endothelial cells exposed to low frequency EF had significantly lower levels of ERK and p38 phosphorylation, as compared to no-EF group, while no differences were detected in phosphorylated JNK levels between low frequency EF and no-EF groups ($p<0.001$, FIG. 5B).

High frequency EF enhances MEK phosphorylation and MEK-cRaf complex formation in endothelial cells.

Figure 6B:
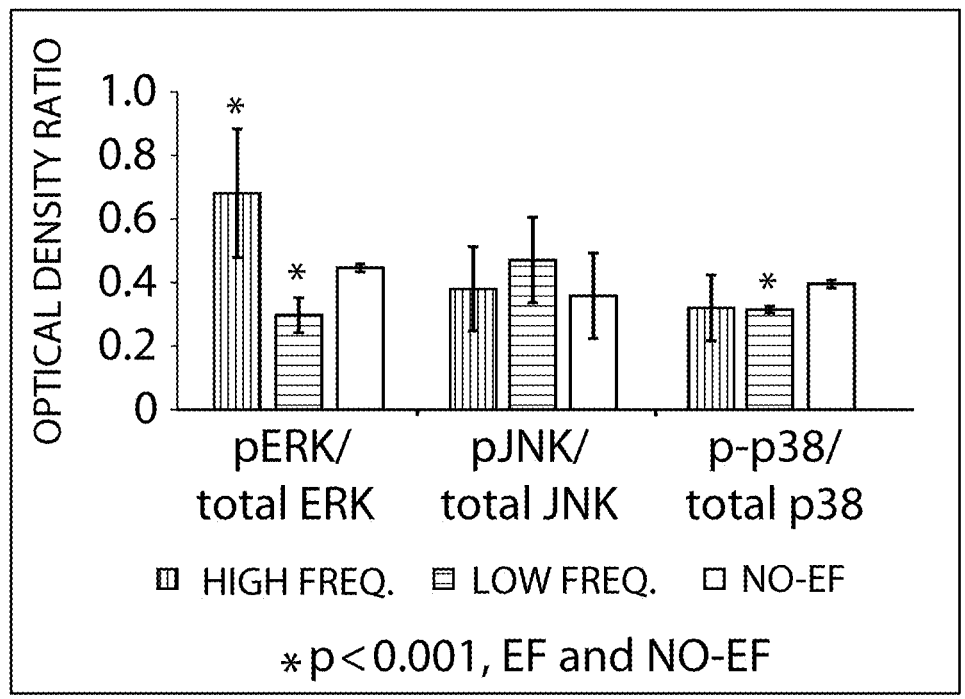
FIG. 6B is a graph demonstrating that high frequency EF increases phosphorylation of ERK but not JNK or p38 and that low frequency ERK significantly decreased the phosphorylation of ERK and p38 when compared with no EF.
Figure 7C:
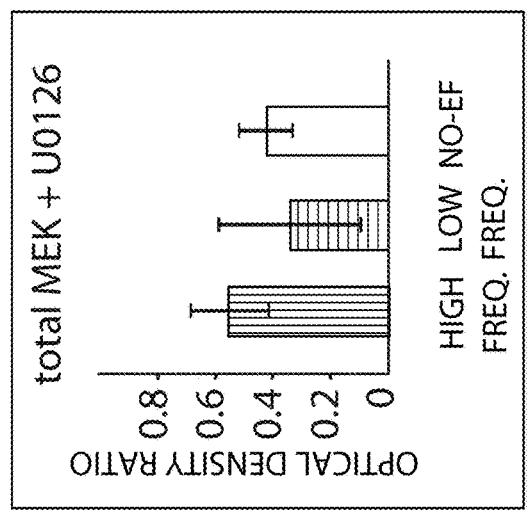
FIG. 7C is a graph demonstrating that the presence of MEK inhibitor U0126 did not affect the total concentration of MEK.
Figure 7B:
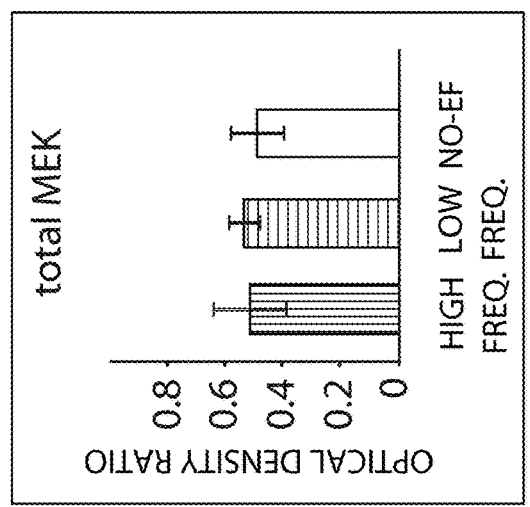
FIG. 7B is a graph demonstrating that high frequency EF did not change the total concentration of MEK.
Figure 7A:
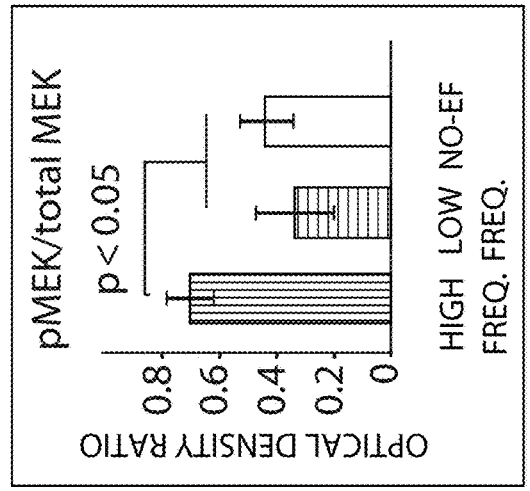
FIG. 7A is a graph demonstrating that high frequency EF significantly increased phosphorylated MEK.
Figures 9A, 9B, 9C:
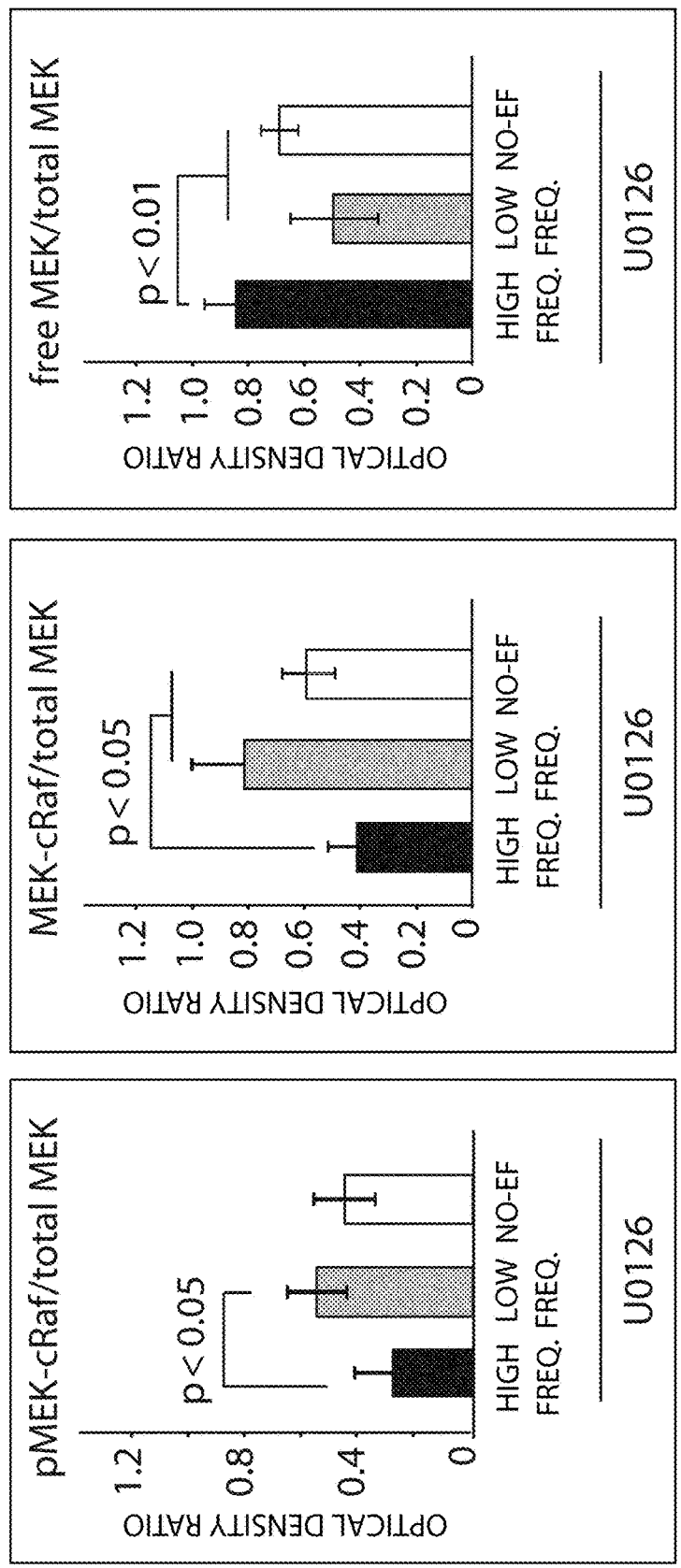
FIG. 9A is a graph demonstrating that MEK inhibitor U0126 significantly decreased pMEK-cRAF complex in high frequency EF compared to controls.
FIG. 9B is a graph demonstrating that MEK inhibitor U0126 significantly decreased MEK-cRAF complex in high frequency EF compared to controls.
FIG. 9C is a graph demonstrating that MEK inhibitor U0126 significantly increased free MEK compared to the low frequency EF and control.

Cell exposure to high frequency EF resulted in significantly higher levels of phosphorylated MEK, while the total MEK levels remained unchanged with EF exposure both in the absence or presence of MEK inhibitor U0126 (FIG. 6A-6C). Previous studies have shown that the binding of upstream cRaf with MEK at Serine 218 and Serine 222 motifs is necessary for MEK phosphorylation and downstream pathway activation. Therefore, to determine the involvement of this MAPK/MEK-ERK pathway in EF-induced angiogenic affects, the levels of cRaf bound to MEK (MEK-cRaf complex), levels of MEK phosphorylation within the complex (pMEK-cRaf) and the free MEK (unbound MEK) levels were quantified. Results showed that cell exposure to high frequency EF significantly increased protein levels and phosphorylation of MEK-cRaf complex, as compared to low frequency or no-EF groups (FIG. 8A-8C, $p<0.001$). This was consistent with low levels of free (unbound) MEK in the high frequency EF group, as compared to those in low frequency and no-EF groups (FIG. 8A-8C, $p<0.05$). In the case of low frequency EF exposure, the free MEK levels were significantly higher than high frequency and no-EF groups ($p<0.05$, FIG. 8A-8C). In contrast to the EF effects observed in the absence of U0126 (FIG. 8A-8C), cell exposure to high frequency EF in the presence of U0126 resulted in reduced protein levels and phosphorylation of MEK-cRaf complex, as well as increased free MEK levels (FIG. 9A-9C, p<0.05), as compared to low frequency or no-EF groups (N=7, p<0.01).

Effects of PI3K, eNOS Inhibition and $Ca^{2+}$ Chelation on EF-Mediated MEK in Phosphorylation in Endothelial Cells.

Figure 10A:
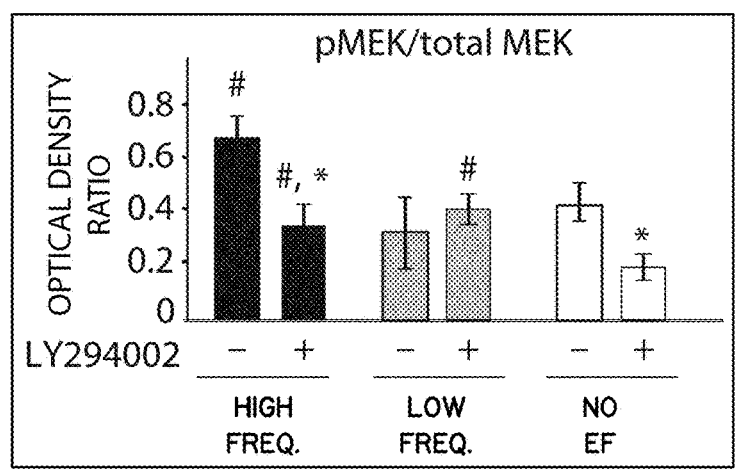
FIG. 10 A is a graph demonstrating that PI3K inhibitor LY294002 did not completely block pMEK stimulatory effect of high frequency EF compared to no EF control.
FIG. 10B is a graph demonstrating that calcium chelator BAPTA resulted in significantly reduced pMEK levels when compared with no-EF controls.
FIG. 10C is a graph demonstrating that L-NAME effectively blocked MEK phosphorylation in high frequency EF group when compared with low frequency and no-EF controls.

PI3K is another upstream mediator of MAPK/MEK pathway, in addition to VEGFR2. Inhibition of PI3K resulted in a significant reduction in the MEK phosphorylation, as expected based on the previous reports. However, stimulatory effect of high frequency EF on MEK phosphorylation was still retained even in the presence of LY294002 (PI3K inhibitor), where pMEK levels were significantly greater in EF groups, as compared to no-EF controls (p<0.05, FIG. 10A).

Figure 10B:
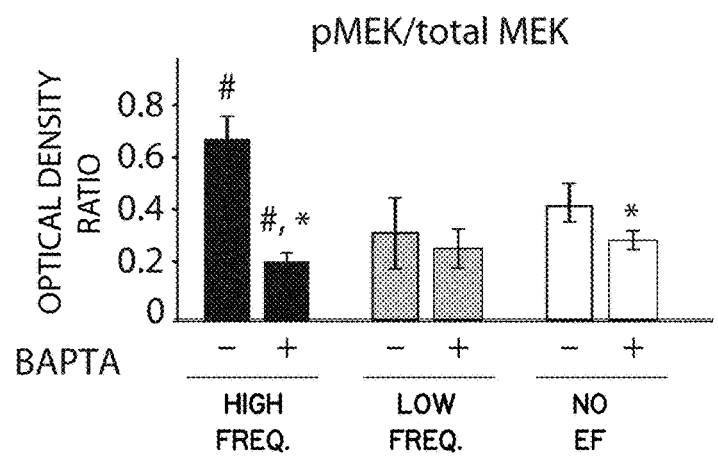

Cell-permeant $Ca^{2+}$-chelating agent BAPTA significantly reduced MEK phosphorylation levels in high frequency EF and no-EF groups (p<0.05, FIG. 10B). Interestingly, the phosphorylated MEK levels were lower in high frequency EF group as compared to no-EF controls in the presence of BAPTA (p<0.05, FIG. 10B), which was similar to the trends in cell responses observed in the presence of MEK inhibitor U0126 (FIGS. 5A, 5B, and 7A-9C) indicating the possible involvement of $Ca^{2+}$ signaling in regulation of MEK pathway activation by high frequency EF. These effects were not observed in low frequency EF groups.

Figure 10C:
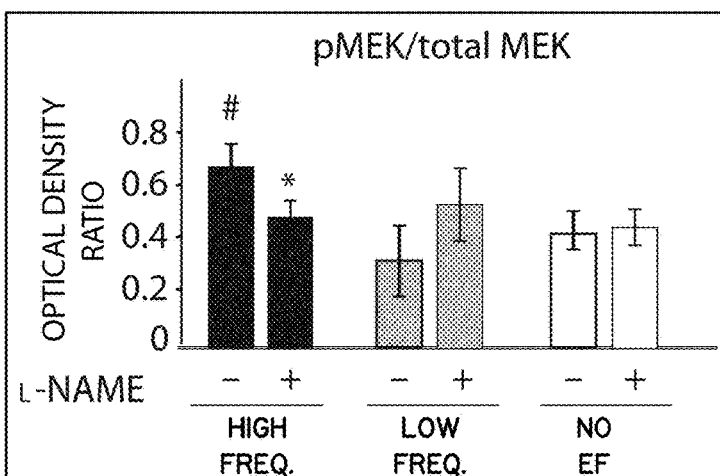
Figure 11:
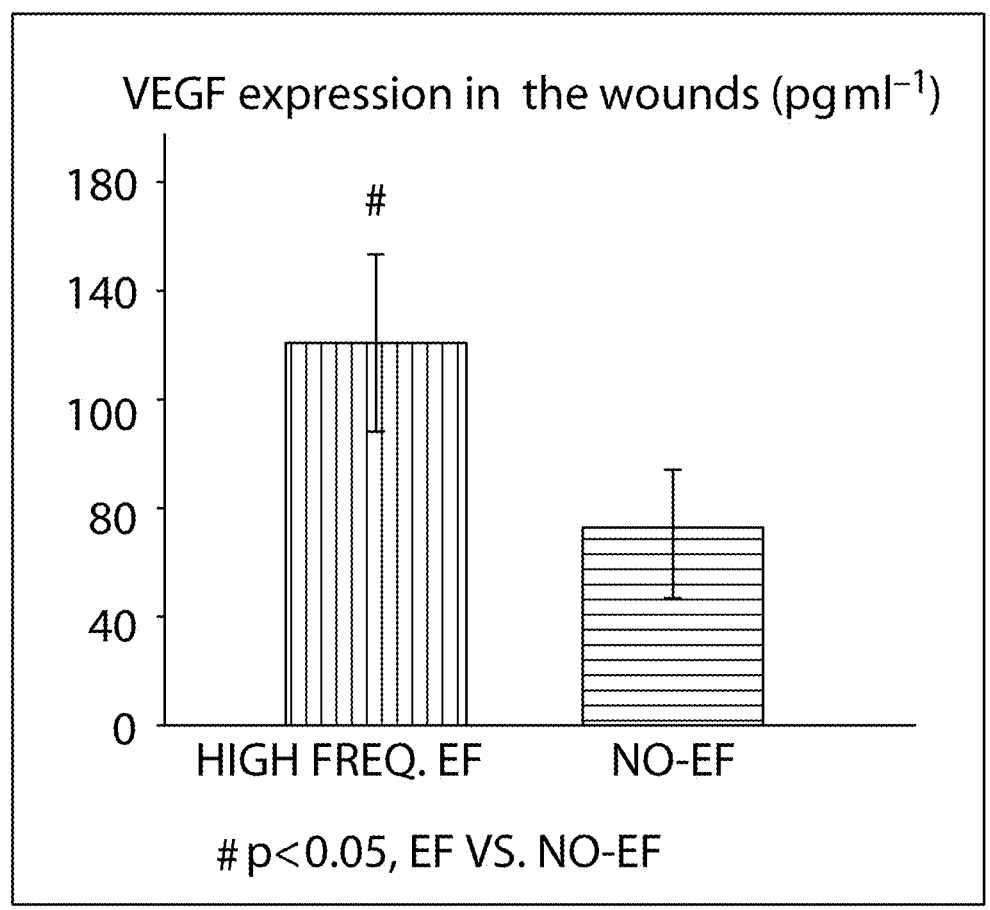
FIG. 11 is a graph demonstrating that in vivo application of high frequency EF (7.5 GHz as 200 mV/mm for 1 h/day for 7 days) to a wound in an animal model of a diabetic animal significantly increased VEGF protein expression.

Pretreatment of endothelial cells with eNOS inhibitor (L-NAME) did not affect the base pMEK levels in no-EF controls (FIG. 10C). However, inhibition of eNOS by L-NAME abolished EF-induced increase in pMEK, suggesting that eNOS signaling may play a partial role in EF-mediated MAPK/ERK pathway activation.

EF exposure did not affect endothelial cell apoptosis or proliferation.

Caspase-3 staining showed no significant effect of EF on endothelial cell apoptosis, with less than 5% apoptotic cells observed in all experimental groups at 12 hours as well as 24 hours of EF exposure. At 12 hours of EF exposure, BrdU staining of endothelial cells indicated a trend of increased cell proliferation with increased frequency, although it was not statistically significant. Also there were no significant differences in the number of proliferating cells after 24 hours of EF exposure.

Figure 12:
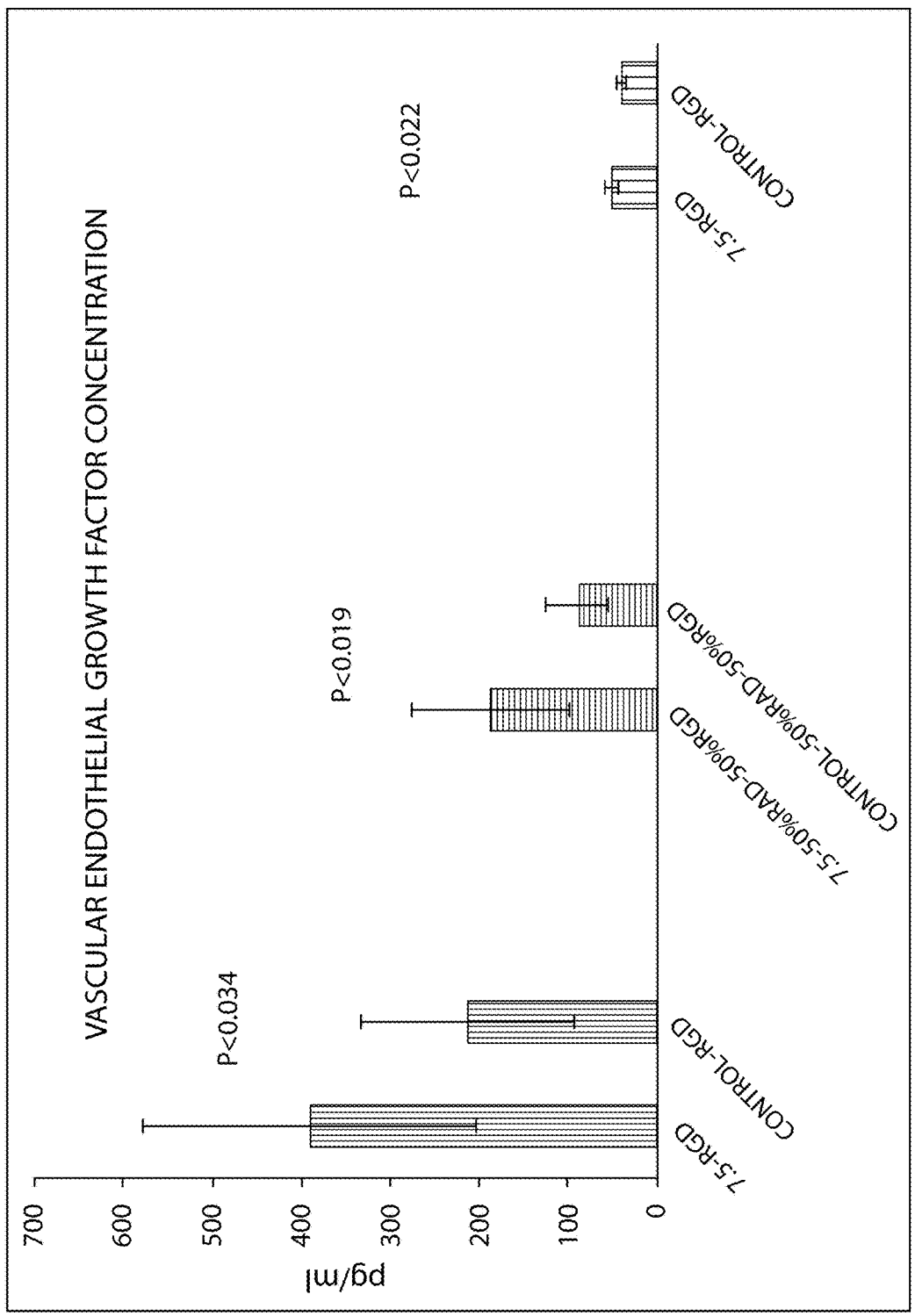
FIG. 12 is a graph demonstrating that in vitro application of high frequency EF (7.5 GHz) to endothelial cells results in increased expression of vascular endothelial growth factor (VEGF) in endothelial cells grown on different types of cell substrate.

As shown in FIG. 12, high-frequency EF (7.5 GHz) stimulation of endothelial cells in vitro results in increased expression of Vascular Endothelial Growth Factor (VEGF).

Figure 13:
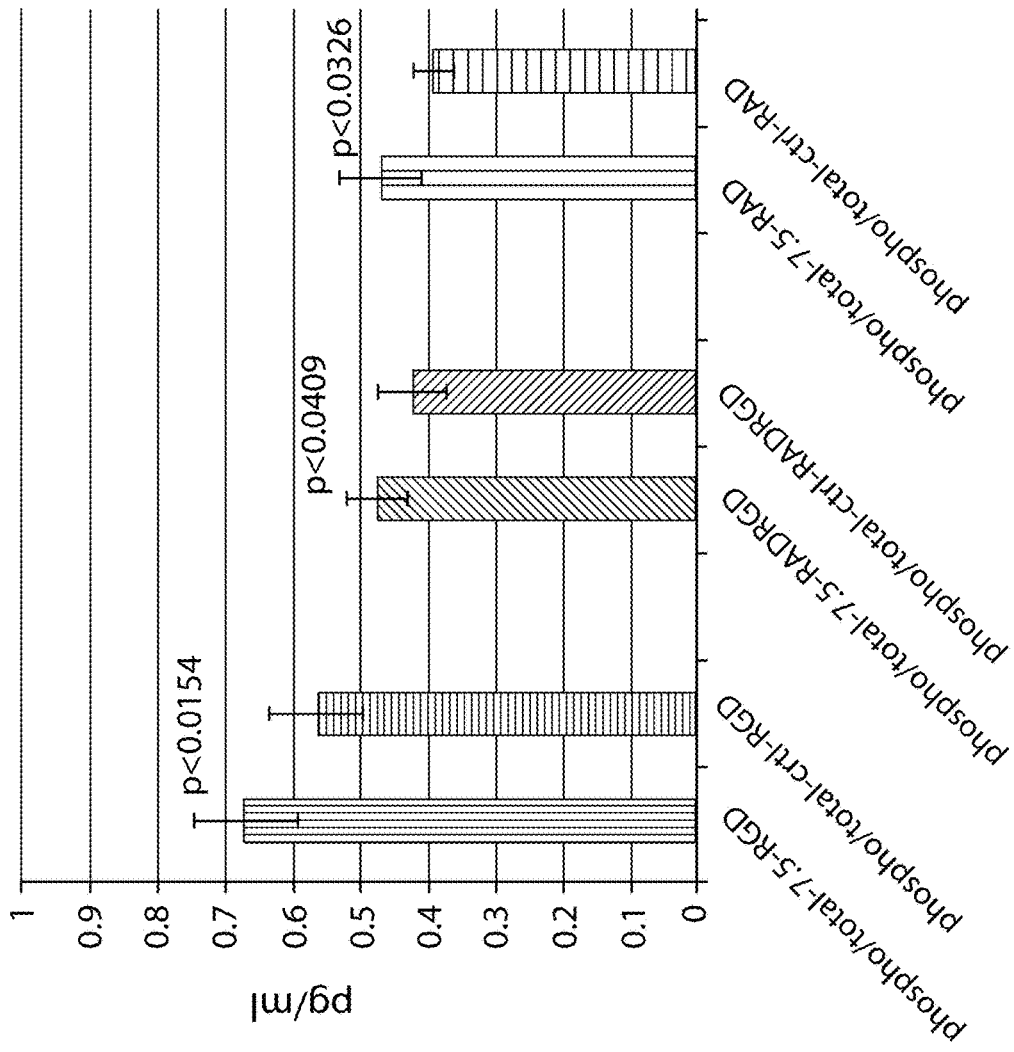
FIG. 13 is a graph demonstrating that in vitro application of high frequency EF stimulated increased expression of focal adhesion kinase (FAK) by microvascular endothelial cells for several types of cell substrates.

High-frequency EF stimulation of endothelial cells in vitro results in increased expression of Focal Adhesion Kinase (FAK), which indicates better communication with the substrate. As shown in FIG. 13, high frequency (7.5 GHz) increased FAK expression in cells grown on, for several different substrates (RAD, RGD, and combinations of RAD and RGD tripeptide substrates).

Figure 14:
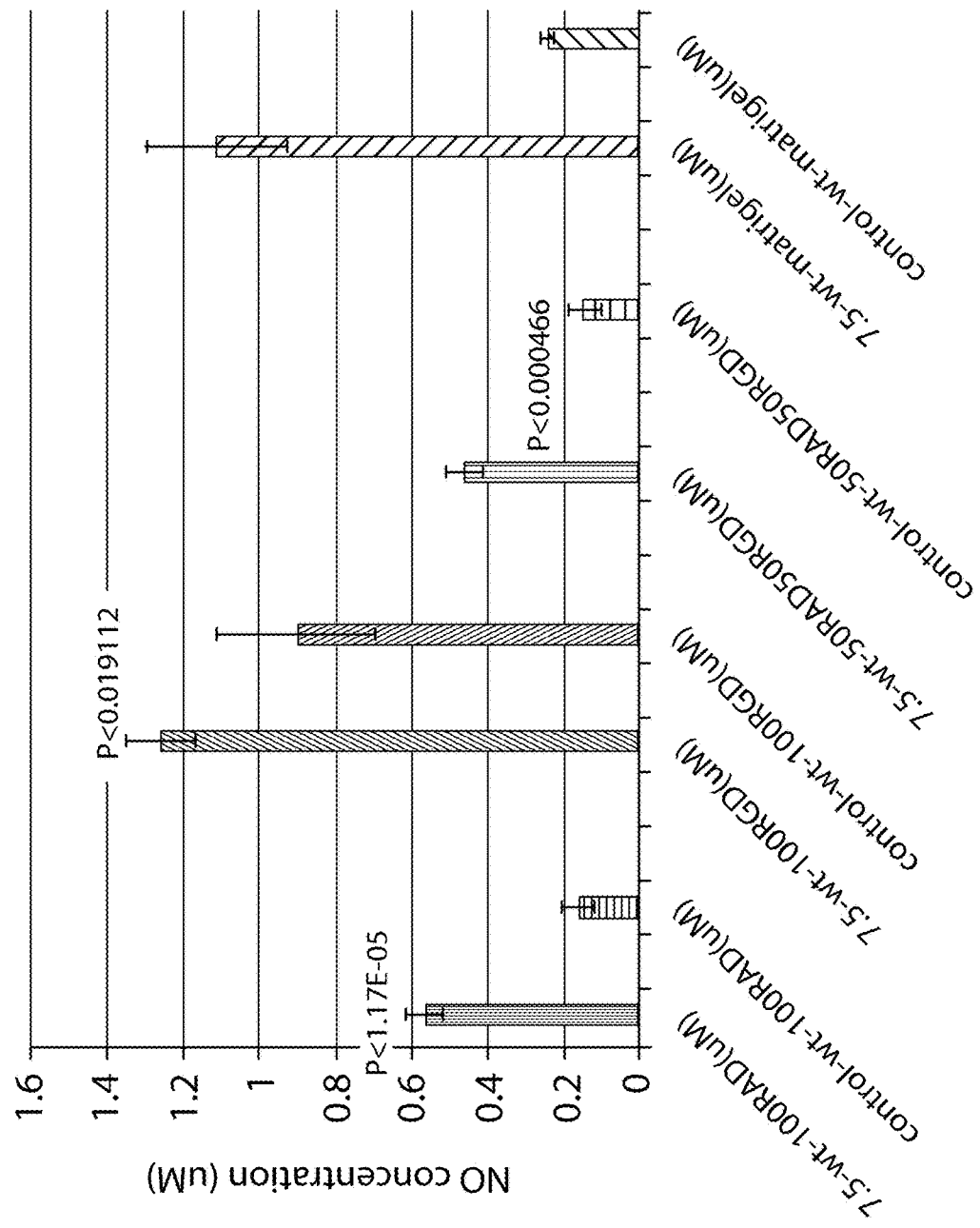
FIG. 14 is a graph demonstrating that in vitro application of high frequency EF stimulated production of nitric oxide (NO) by microvascular endothelial cells suggesting enhanced endothelial cell function for several different cell substrates.

High-frequency EF (7.5 GHz) stimulation of endothelial cells in vitro results in increased release of NO for cells cultured on several different substrates, indicating enhanced endothelial function (FIG. 14).

In Vivo EF Exposure Enhances VEGF Expression in Diabetic Wounds

For a preliminary in vivo validation of the in vitro results, a mouse db/db model of diabetic wound healing was used. Wound treatment with high-frequency EF resulted in significantly increased VEGF protein levels in the wound tissue as compared to no-EF treated control wounds (FIG. 10). No detrimental effects of EF exposure on wound healing were observed during EF treatment. Importantly, previous studies demonstrated that increased VEGF expression results in improved healing in diabetic wounds, suggesting that high-frequency EF therapy has therapeutic potential.

In vivo studies of wound healing demonstrate that wounds on diabetic mice had improved healing characteristic when exposed to a high frequency electric field of 7.5 GHz applied at 200 mV/mm for 1 hour per day for 7 days when compared to a control wound on the same animals that was not exposed to the electric field. Compared to the control wound, the epithelial gap of the HF exposed wound was significantly smaller (about 2 mm compared to about 3.8 mm), the area of granulation was increased (about 1 $mm^2$ compared to about 0.5 $mm^2$) and VEGF expression was increased (about 130 pg/ml compared to about 75 pg/ml).

Figure 15A:
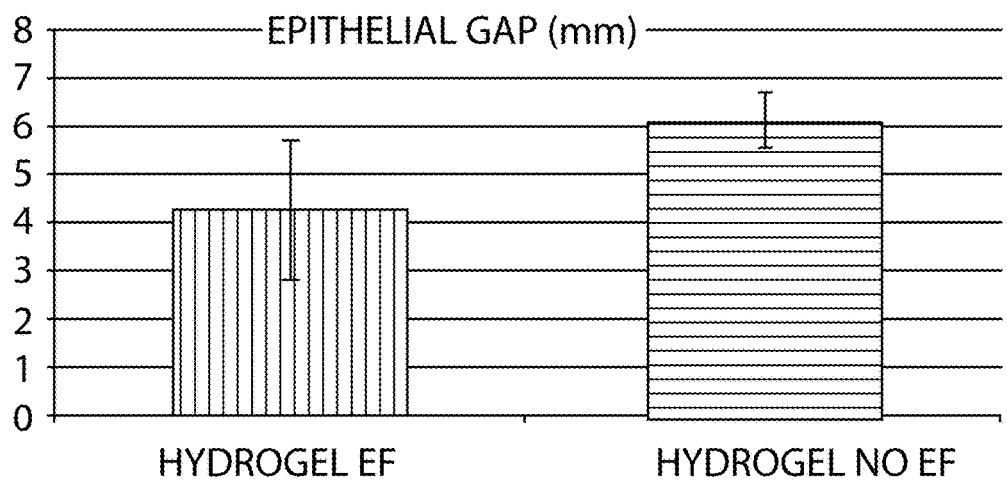
FIG. 15A is a graph demonstrating that in vivo application of high frequency EF (7.5 GHz as 200 mV/mm for 1 h/day for 7 days) in combination with a hydrogel treatment significantly decreased the epithelial gap in the wound.
Figure 15B:
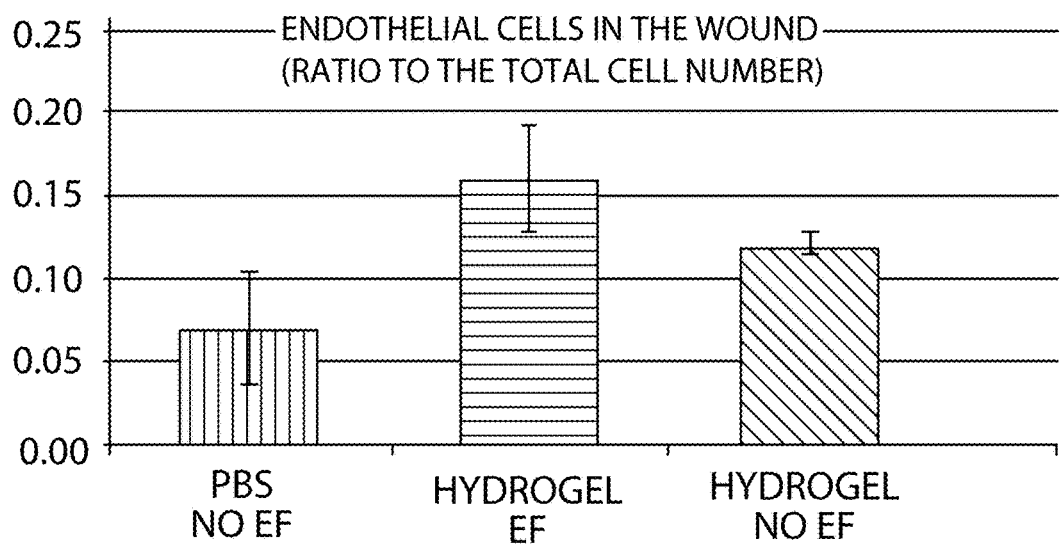
FIG. 15B is a graph demonstrating that in vivo application of high frequency EF in combination with hydrogel treatment increased endothelial cells in the wound when compared with no treatment or hydrogel treatment alone.

Additional studies conducted with the combination of high frequency EF and a hydrogel wound treatment resulted in improved wound healing as compared to EF or hydrogel alone. As seen in FIG. 15A, the epithelial gap decreased in animals treated with a combination of EF and hydrogel as compared to treatment with the hydrogel alone. FIG. 15B demonstrates that the combination of EF and hydrogel increases the ratio of endothelial cells in the wound as compared to either no EF/no hydrogel and hydrogel alone. These data demonstrate that the wound healing effects of EF and hydrogel treatments may be combined to further improve wound healing.

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be made from such details without departing from the general inventive concept.

What is claimed is:

1. A method of treating a wound in a tissue, the method comprising:
    covering the wound with a dressing consisting of a hydrogel; and
    exposing the tissue having the wound to a high frequency electric field at a frequency in a range between 1 GHz and 10 GHz
    continuously for a duration of at least 20 minutes per day in a non-thermal manner to induce wound healing.

2. The method of claim 1 wherein the wound is a chronic wound.

3. The method of claim 1 wherein the wound is a diabetic wound, a bed sore, or a hypoxia induced wound.

4. The method of claim 1 wherein the high frequency electric field is in a range between 5 GHz and 8 GHz.

5. The method of claim 1 wherein the high frequency electric field is about 7.5 GHz.

6. The method of claim 1 wherein the duration is at least 60 minutes per day.

7. The method of claim 1 wherein the duration is at least 2 hours per day.

8. The method of claim 1 wherein the tissue is exposed to the high frequency electric field for up to 12 weeks.

9. The method of claim 1 wherein the method is applied at an ambient pressure.

10. A method of inducing angiogenesis in a tissue, the method comprising:
    covering the wound with a dressing consisting of a hydrogel; and
    exposing the tissue having the wound to a high frequency electric field at a frequency in a range between 1 GHz and 10 GHz
    continuously for a duration of at least 20 minutes per day in a non-thermal manner to induce angiogenesis,
    wherein the method is applied at an ambient pressure.

11. The method of claim 10 wherein the high frequency electric field is in a range between 5 GHz and 8 GHz.

12. The method of claim 10 wherein the high frequency electric field is about 7.5 GHz.

13. The method of claim 10 wherein the duration is at least 60 minutes per day.

14. The method of claim 10 wherein the duration is at least 2 hours per day.

15. The method of claim 10 wherein the tissue is exposed to the high frequency electric field for up to 12 weeks.

16. A method of inducing MAPK/ERK pathway activation in a tissue, the method comprising:
    covering the wound with a dressing consisting of a hydrogel; and
    exposing the tissue having the wound to a high frequency electric field at a frequency in a range between 1 GHz and 10 GHz
    continuously for a duration of at least 20 minutes per day in a non-thermal manner to induce MAPK/ERK pathway activation.

17. The method of claim 16 wherein the duration is at least 60 minutes per day.

18. The method of claim 16 wherein the duration is at least 2 hours per day.

19. A method of inducing nitric oxide (NO) production in a tissue consisting of exposing the tissue having the wound to a high frequency electric field at a frequency in a range between 1 GHz and 10 GHz and exposing continuously for a duration of at least 20 minutes per day to induce NO production.

20. A method of inducing Vascular Endothelial Growth Factor (VEGF) production in a tissue, the method consisting of:
    covering the wound with a dressing consisting of a hydrogel; and
    exposing the tissue having the wound to a high frequency electric field at a frequency in a range between 1 GHz and 10 GHz
    continuously for a duration of at least 20 minutes per day in a non-thermal manner to induce VEGF production.

* * * * *